US010932767B2

(12) United States Patent
Naga Kalepu et al.

(10) Patent No.: US 10,932,767 B2
(45) Date of Patent: Mar. 2, 2021

(54) SURGICAL ACCESS ASSEMBLY AND METHOD OF USE THEREFOR

(71) Applicant: Covidien LP, Mansfield, MA (US)

(72) Inventors: Hari Naga Kalepu, Hyderabad (IN); Sabastian George, Hyderabad (IN); Raja Kamaraj, Hyderabad (IN)

(73) Assignee: Covidien LP, Mansfield, MA (US)

( * ) Notice: Subject to any disclaimer, the term of this patent is extended or adjusted under 35 U.S.C. 154(b) by 61 days.

(21) Appl. No.: 16/213,329

(22) Filed: Dec. 7, 2018

(65) Prior Publication Data

US 2020/0178949 A1 Jun. 11, 2020

(51) Int. Cl.
*A61B 17/02* (2006.01)
*A61M 13/00* (2006.01)
*A61B 17/00* (2006.01)

(52) U.S. Cl.
CPC ...... *A61B 17/0218* (2013.01); *A61B 17/0293* (2013.01); *A61M 13/003* (2013.01); *A61B 2017/00477* (2013.01); *A61B 2017/00862* (2013.01); *A61B 2017/0225* (2013.01)

(58) Field of Classification Search
CPC . A61B 17/02; A61B 17/0218; A61B 17/0293; A61B 17/0281; A61B 2017/0225
See application file for complete search history.

(56) References Cited

U.S. PATENT DOCUMENTS

| | | |
|---|---|---|
| 4,183,357 A | 1/1980 | Bentley et al. |
| 4,984,564 A | 1/1991 | Yuen |
| 5,366,478 A | 11/1994 | Brinkerhoff et al. |

(Continued)

FOREIGN PATENT DOCUMENTS

| | | |
|---|---|---|
| EP | 0950376 A1 | 10/1999 |
| EP | 1707235 A1 | 10/2006 |

(Continued)

OTHER PUBLICATIONS

Demetrius E.M. Litwin, et al. "Hand-Assisted Laparoscopic Surgery (HALS) With the HandPort System", Annals of Surgery, May 2000; 231(5): 715-723; https://www.ncbi.nlm.nih.gov/pmc/articles/PMC1421059/.

(Continued)

*Primary Examiner* — Ellen C Hammond
(74) *Attorney, Agent, or Firm* — Carter DeLuca & Farrell LLP

(57) ABSTRACT

A surgical access assembly includes a sleeve assembly, a base member, and a sealing assembly. The sleeve assembly includes a proximal ring, a distal ring, and a sleeve defining a passage therethrough. The base member includes an annular body including a coupling member. The annular body defines an opening in communication with the passage of the sleeve, and a circumferential groove configured to support the proximal ring of the sleeve assembly. The sealing assembly includes an annular frame and a seal dimensioned to cover the opening of the base member in a sealing relation. The coupling member of the base member releasably secures the sealing assembly to the base member. The annular frame of the sealing assembly is configured to be in registration with the annular body of the base member such that the proximal ring is interposed between the base member and the sealing assembly.

11 Claims, 5 Drawing Sheets

(56) References Cited

U.S. PATENT DOCUMENTS

| | | |
|---|---|---|
| 5,520,609 A | 5/1996 | Moll et al. |
| 5,524,644 A | 6/1996 | Crook |
| 5,649,550 A | 7/1997 | Crook |
| 5,735,791 A | 4/1998 | Alexander, Jr. et al. |
| 5,741,298 A | 4/1998 | MacLeod |
| 5,803,921 A | 9/1998 | Bonadio |
| 5,899,208 A | 5/1999 | Bonadio |
| 5,906,577 A | 5/1999 | Beane et al. |
| 6,033,426 A | 3/2000 | Kaji |
| 6,033,428 A | 3/2000 | Sardella |
| 6,142,936 A | 11/2000 | Beane et al. |
| 6,254,534 B1 | 7/2001 | Butler et al. |
| 6,382,211 B1 | 5/2002 | Crook |
| 6,450,983 B1 | 9/2002 | Rambo |
| 6,558,371 B2 | 5/2003 | Dorn |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,723,044 B2 | 4/2004 | Pulford et al. |
| 6,846,287 B2 | 1/2005 | Bonadio et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 7,033,319 B2 | 4/2006 | Pulford et al. |
| 7,081,089 B2 | 7/2006 | Bonadio et al. |
| 7,153,261 B2 | 12/2006 | Wenchell |
| 7,163,510 B2 * | 1/2007 | Kahle ............... A61B 17/3423 600/208 |
| 7,195,590 B2 | 3/2007 | Butler et al. |
| 7,238,154 B2 | 7/2007 | Ewers et al. |
| 7,344,547 B2 | 3/2008 | Piskun |
| 7,377,898 B2 | 5/2008 | Ewers et al. |
| 7,445,597 B2 | 11/2008 | Butler et al. |
| 7,473,221 B2 | 1/2009 | Ewers et al. |
| 7,540,839 B2 | 6/2009 | Butler et al. |
| 7,559,893 B2 | 7/2009 | Bonadio et al. |
| 7,650,887 B2 | 1/2010 | Nguyen et al. |
| 7,704,207 B2 | 4/2010 | Albrecht et al. |
| 7,727,146 B2 | 6/2010 | Albrecht et al. |
| 7,736,306 B2 | 6/2010 | Brustad et al. |
| 7,909,760 B2 | 3/2011 | Albrecht et al. |
| 7,951,076 B2 | 5/2011 | Hart et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,142,354 B1 | 3/2012 | Larson et al. |
| 8,187,177 B2 * | 5/2012 | Kahle ............... A61B 5/0507 600/208 |
| 8,187,178 B2 | 5/2012 | Bonadio et al. |
| 8,231,527 B2 | 7/2012 | Beckman et al. |
| 8,273,017 B1 | 9/2012 | Moreno |
| 8,343,047 B2 | 1/2013 | Albrecht et al. |
| 8,353,824 B2 | 1/2013 | Shelton, IV et al. |
| 8,357,085 B2 | 1/2013 | Shelton, IV et al. |
| 8,357,086 B2 * | 1/2013 | Kahle ............... A61B 17/3423 600/208 |
| 8,414,485 B2 | 4/2013 | Richard et al. |
| 8,550,992 B2 | 10/2013 | Kleyman |
| 8,574,153 B2 | 11/2013 | Richard |
| 8,602,983 B2 | 12/2013 | Kleyman |
| 8,845,529 B2 | 9/2014 | Smith |
| 9,017,249 B2 | 4/2015 | Smith |
| 9,144,422 B2 | 9/2015 | Smith |
| 9,149,178 B2 | 10/2015 | Smith |
| 9,474,519 B2 | 10/2016 | Brustad et al. |
| 2001/0037053 A1 | 11/2001 | Bonadio et al. |
| 2003/0139767 A1 | 7/2003 | Jespersen |
| 2003/0187376 A1 | 10/2003 | Rambo |
| 2004/0092795 A1 | 5/2004 | Bonadio et al. |
| 2004/0154624 A1 | 8/2004 | Bonadio et al. |
| 2004/0267096 A1 | 12/2004 | Caldwell et al. |
| 2005/0020884 A1 | 1/2005 | Hart et al. |
| 2005/0059865 A1 * | 3/2005 | Kahle ............... A61B 5/6898 600/206 |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0222582 A1 | 10/2005 | Wenchell |
| 2005/0241647 A1 | 11/2005 | Nguyen et al. |
| 2005/0288558 A1 | 12/2005 | Ewers et al. |
| 2006/0084842 A1 | 4/2006 | Hart et al. |
| 2006/0161049 A1 | 7/2006 | Beane et al. |
| 2006/0161050 A1 | 7/2006 | Butler et al. |
| 2006/0247498 A1 | 11/2006 | Bonadio et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0162067 A1 | 7/2007 | Lunsford et al. |
| 2007/0203398 A1 | 8/2007 | Bonadio et al. |
| 2007/0208312 A1 | 9/2007 | Norton et al. |
| 2007/0270654 A1 | 11/2007 | Pignato et al. |
| 2008/0011307 A1 | 1/2008 | Beckman et al. |
| 2008/0021360 A1 | 1/2008 | Fihe et al. |
| 2008/0021362 A1 | 1/2008 | Fihe et al. |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0221607 A1 | 9/2008 | White et al. |
| 2009/0221966 A1 | 9/2009 | Richard |
| 2010/0113883 A1 | 5/2010 | Widenhouse et al. |
| 2010/0240960 A1 | 9/2010 | Richard |
| 2010/0249516 A1 | 9/2010 | Shelton, IV et al. |
| 2010/0249520 A1 | 9/2010 | Shelton, IV et al. |
| 2010/0249521 A1 | 9/2010 | Shelton, IV et al. |
| 2010/0249525 A1 | 9/2010 | Shelton, IV et al. |
| 2010/0261972 A1 | 10/2010 | Widenhouse et al. |
| 2010/0261973 A1 | 10/2010 | Mollenauer et al. |
| 2010/0261974 A1 | 10/2010 | Shelton, IV et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0312066 A1 | 12/2010 | Cropper et al. |
| 2011/0054260 A1 | 3/2011 | Albrecht et al. |
| 2011/0066001 A1 | 3/2011 | Shelton et al. |
| 2011/0125186 A1 | 5/2011 | Fowler et al. |
| 2011/0201883 A1 | 8/2011 | Cooper et al. |
| 2011/0251463 A1 | 10/2011 | Kleyman |
| 2011/0251464 A1 | 10/2011 | Kleyman |
| 2012/0130177 A1 | 5/2012 | Davis |
| 2012/0130186 A1 | 5/2012 | Stopek et al. |
| 2012/0130187 A1 | 5/2012 | Okoniewski |
| 2012/0157779 A1 | 6/2012 | Fischvogt |
| 2012/0157781 A1 | 6/2012 | Kleyman |
| 2012/0157786 A1 | 6/2012 | Pribanic |
| 2012/0190933 A1 | 7/2012 | Kleyman |
| 2012/0209078 A1 | 8/2012 | Pribanic et al. |
| 2012/0238825 A1 | 9/2012 | Smith |
| 2012/0245427 A1 | 9/2012 | Kleyman |
| 2012/0245428 A1 | 9/2012 | Smith et al. |
| 2012/0245429 A1 | 9/2012 | Smith |
| 2012/0245430 A1 | 9/2012 | Kleyman et al. |
| 2012/0253134 A1 | 10/2012 | Smith |
| 2012/0253136 A1 | 10/2012 | Rodrigues, Jr. |
| 2012/0283520 A1 | 11/2012 | Kleyman |
| 2013/0172681 A1 | 7/2013 | Smith |
| 2013/0253277 A1 | 9/2013 | Smith |
| 2013/0253278 A1 | 9/2013 | Smith |
| 2013/0253279 A1 | 9/2013 | Smith |
| 2018/0271508 A1 | 9/2018 | Berti et al. |

FOREIGN PATENT DOCUMENTS

| | | |
|---|---|---|
| EP | 2090259 A1 | 8/2009 |
| EP | 2181657 A2 | 5/2010 |
| EP | 2238926 A2 | 10/2010 |
| EP | 2238933 A1 | 10/2010 |
| EP | 3020347 A1 | 5/2016 |
| WO | 9610963 A1 | 4/1996 |
| WO | 0032116 | 6/2000 |
| WO | 0054675 | 9/2000 |
| WO | 0191652 A1 | 12/2001 |
| WO | 2004075741 A2 | 9/2004 |

(56) References Cited

FOREIGN PATENT DOCUMENTS

| WO | 2006110733 | A2 | 10/2006 |
| WO | 2010141409 | A1 | 12/2010 |
| WO | 2010141673 | A1 | 12/2010 |

OTHER PUBLICATIONS

European Search Report dated Apr. 24, 2013 from European Application No. 12198750.7. (4 pgs.).
European Search Report from EP 13160771 dated Jun. 10, 2014.
Extended European Search Report issued in European Patent Application No. 19214094.5, dated Feb. 20, 2020.

* cited by examiner

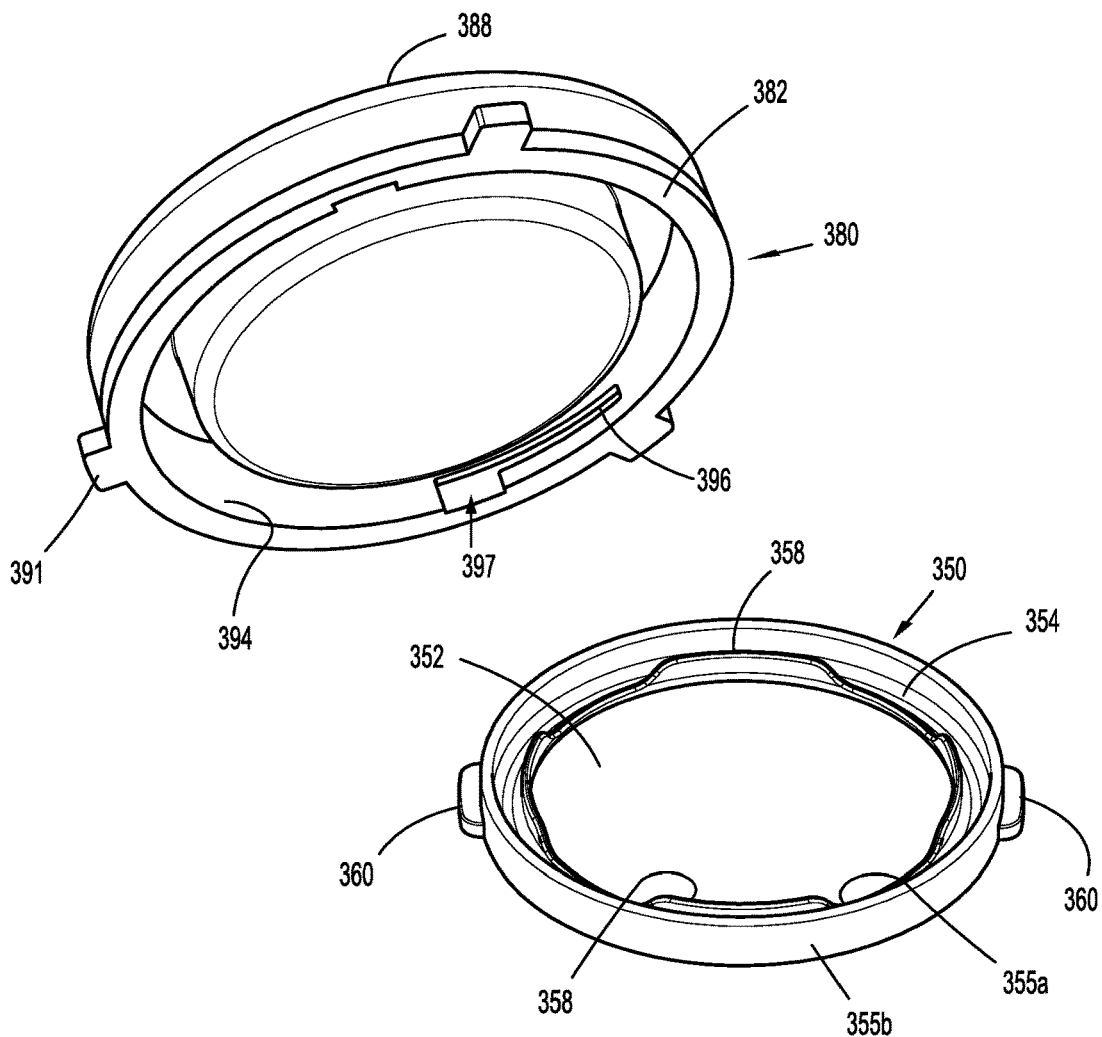
FIG. 9
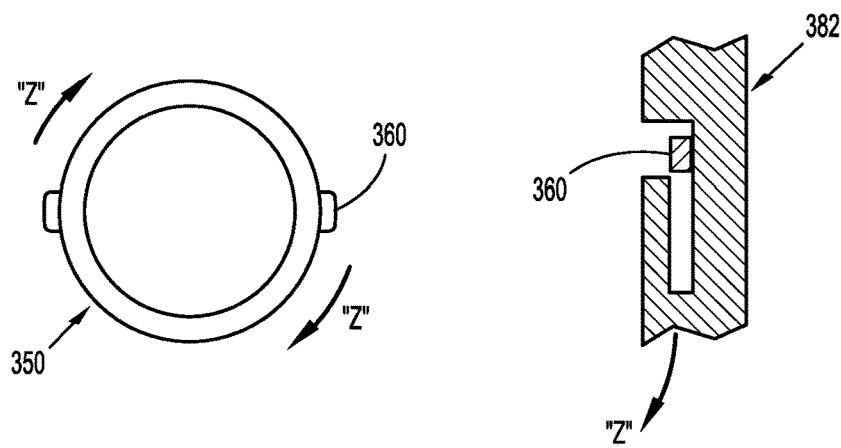
FIG. 10  FIG. 11

SURGICAL ACCESS ASSEMBLY AND METHOD OF USE THEREFOR

BACKGROUND

Technical Field

The present disclosure relates to a surgical access assembly, and more particularly, to a surgical access assembly including a sleeve assembly and a sealing assembly adaptably engaging each other in a sealing relation and a method of use therefor.

Background of Related Art

Various surgical procedures are performed in a minimally invasive manner. This includes forming a small opening through a body wall of the patient, e.g., in the abdomen, and inserting a seal anchor through the opening to provide a substantially fluid-tight seal between a body cavity of a patient and the atmosphere. Due to the relatively small interior dimensions of the access devices used in endoscopic procedures, only the elongated, small diametered instrumentation such as, e.g., trocar and cannula assemblies, may be used to access the internal body cavities and organs.

However, minimally invasive surgery such as, e.g., laparoscopy, has several limitations. In particular, surgery of this type requires a great deal of skill in manipulating the long narrow endoscopic instruments to a remote site under endoscopic visualization. To this end, hand-assisted laparoscopic techniques and procedures have been developed. These procedures include both laparoscopic and conventional surgical methodologies. The hand-assisted technique is performed utilizing a seal anchor in conjunction with a sleeve assembly, which is an enlarged device that protects the incised opening from, for example, infection and contamination. In general, prior to the introduction of the surgical object into the patient's body, insufflation gases are used to enlarge the area surrounding the target surgical site to create a larger, more accessible work area.

The maintenance of a substantially fluid-tight seal is desirable to inhibit the escape of the insufflation gases and the deflation or collapse of the enlarged surgical site. Accordingly, there is a need for a surgical access assembly used in a hand-assisted minimally invasive procedure that can maintain the integrity of an insufflated workspace.

SUMMARY

In accordance with an embodiment of the present disclosure, a surgical access assembly includes a sleeve assembly, a base member, and a sealing assembly. The sleeve assembly includes a proximal ring, a distal ring, and a sleeve defining a passage therethrough. The sleeve extends between the proximal and distal rings. The base member includes an annular body including a coupling member. The annular body defines an opening in communication with the passage of the sleeve, and a circumferential groove configured to support the proximal ring of the sleeve assembly. The sealing assembly includes an annular frame and a seal dimensioned to cover the opening of the base member in a sealing relation. The coupling member of the base member releasably secures the sealing assembly to the base member. The annular frame of the sealing assembly is configured to be in registration with the annular body of the base member such that the proximal ring is interposed between the base member and the sealing assembly.

In an embodiment, the seal may include a body configured to be received in the opening of the base member and an overhang extending radially outward from the body.

In another embodiment, the annular frame and the body of the seal may define a gap therebetween. The gap may be dimensioned to receive at least a portion of the proximal ring of the sleeve assembly.

In yet another embodiment, the annular body of the base member may include lips disposed radially inward of the proximal ring of the sleeve assembly. The lips may be configured to retain the proximal ring within the circumferential groove of the annular body.

In an embodiment, the sealing assembly may be hingedly coupled with the base member. In particular, the annular frame of the sealing assembly may include a hook. The annular body of the base member may define an aperture dimensioned to receive the hook.

In another embodiment, the hook may be deflectable such that the hook is selectably movable through the aperture of the base member.

In an embodiment, the seal of the sealing assembly may be formed of gel or silicone.

In another embodiment, the proximal ring of the sleeve assembly may have a kidney-shaped cross-section.

In yet another embodiment, the sleeve of the sleeve assembly may be rollable about the proximal ring.

In still yet another embodiment, the annular body of the base member may include a first planar surface extending radially outward from the circumferential groove, and the annular frame of the sealing assembly may include a second planar surface configured to be in planar contact with the first planar surface when the base member and the sealing assembly are in registration with each other.

In another embodiment, the annular body of the base member may include a fastening member extending proximally from the first planar surface, and the second planar surface of the sealing assembly may define a slot dimensioned to receive the fastening member.

In an embodiment, at least one of the fastening member of the base member or the second planar surface of the sealing assembly may be formed of an elastic material.

In another embodiment, the annular frame of the sealing assembly may include a support disposed radially inward of the second planar surface.

In an embodiment, the seal may be over-molded onto the support.

In another embodiment, the base member may include a tab on an outer wall thereof, and the annular frame may define a slot dimensioned to slidably rotate the sealing assembly relative to the base member.

In yet another embodiment, the annular frame may further define an axially extending notch in communication with the slot. The axially extending notch may be configured to lead the tab of the base member into the slot of the annular frame.

In accordance with another aspect of the present disclosure, a method of accessing an internal body cavity includes positioning a sleeve assembly at least partially in the internal body cavity; rolling a sleeve of the sleeve assembly such that proximal and distal portions of the sleeve assembly engage an outer epidermal tissue and an internal peritoneal wall of tissue, respectively; placing a proximal ring of the sleeve assembly in a circumferential groove defined in a base member; placing a sealing assembly in registration with the base member such that a body portion of a seal of the sealing assembly covers an opening defined in the base member in sealing relation, and an overhang of the seal extending radially outward from the body portion of the seal engages the proximal ring of the sleeve assembly; releasably securing the sealing assembly with the base member; and introducing an object into the internal body cavity through the sealing assembly.

In an embodiment, releasably securing the sealing assembly with the base member may include hingedly coupling the sealing assembly with the base member.

In another embodiment, releasably securing the sealing assembly with the base member may include rotating the sealing assembly relative to the base member by placing a tab on an outer wall of the base member into a circumferential slot defined in an inner wall of the sealing assembly.

In yet another embodiment, releasably securing the sealing assembly with the base member may include placing a fastener extending proximally from the base member into a slot defined in the sealing assembly.

In still yet another embodiment, the method may further include insufflating the internal body cavity.

BRIEF DESCRIPTION OF THE DRAWINGS

Various embodiments of the present disclosure are described hereinbelow with reference to the drawings, wherein:

FIG. 9 is a perspective view of a sealing assembly and a base member in accordance with another embodiment of the present disclosure;

FIG. 10 is a top view of the base member of FIG. 9; and

FIG. 11 is a partial cross-sectional view of the sealing assembly and the base member of FIG. 9, illustrating a locking mechanism.

DETAILED DESCRIPTION OF EMBODIMENTS

Figure 1:
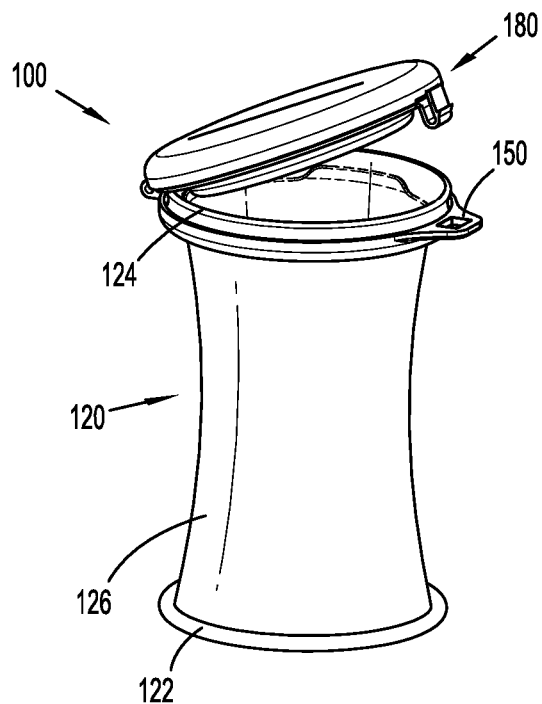
FIG. 1 is a perspective view of a surgical access assembly in accordance with an embodiment of the present disclosure, illustrating an open state.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, there is illustrated a surgical access assembly 100 in accordance with an embodiment of the present disclosure. The surgical access assembly 100 is configured to receive an object such as, e.g., a hand of a clinician, while maintaining the integrity of an insufflated workspace. The surgical access assembly 100 includes a sleeve assembly 120, a base member 150, and a sealing assembly 180. The sleeve assembly 120 is adapted for insertion within a tissue tract, e.g., through an opening in the abdominal or peritoneal lining, as well as a naturally occurring orifice. The sleeve assembly 120 protects the opening from, for example, infection and contamination. The base member 150 is configured to support the sleeve assembly 120. The sealing assembly 180 is configured to be releasably coupled with the base member 150. Such a configuration enhances integrity of an insufflated workspace by inhibiting, e.g., inadvertent detachment, of the sleeve assembly 120 from the sealing assembly 180.

With continued reference to FIG. 1, the sleeve assembly 120 includes a distal ring 122, a proximal ring 124, and a flexible sleeve 126 defining a passage therethrough. The distal and proximal rings 122, 124 are concentrically arranged and are connected to opposing ends of the sleeve 126. The distal and proximal rings 122, 124 are formed of relatively flexible materials to facilitate compression and expansion of the distal and proximal rings 122, 124. For example, the distal and proximal rings 122, 124 may be made from an elastomer such as polyurethane, polyethylene, silicone, and the like. The resilient nature of the distal and proximal rings 122, 124 allows the distal and proximal rings 122, 124 to return to their normal, substantially annular configuration after compression or deformation by the clinician. In particular, the distal and proximal rings 122, 124 are adapted to engage the walls defining the body cavity. The distal ring 122 is configured to engage the internal peritoneal wall, and the proximal ring 124 is configured to engage the outer epidermal tissue.

Figure 4:
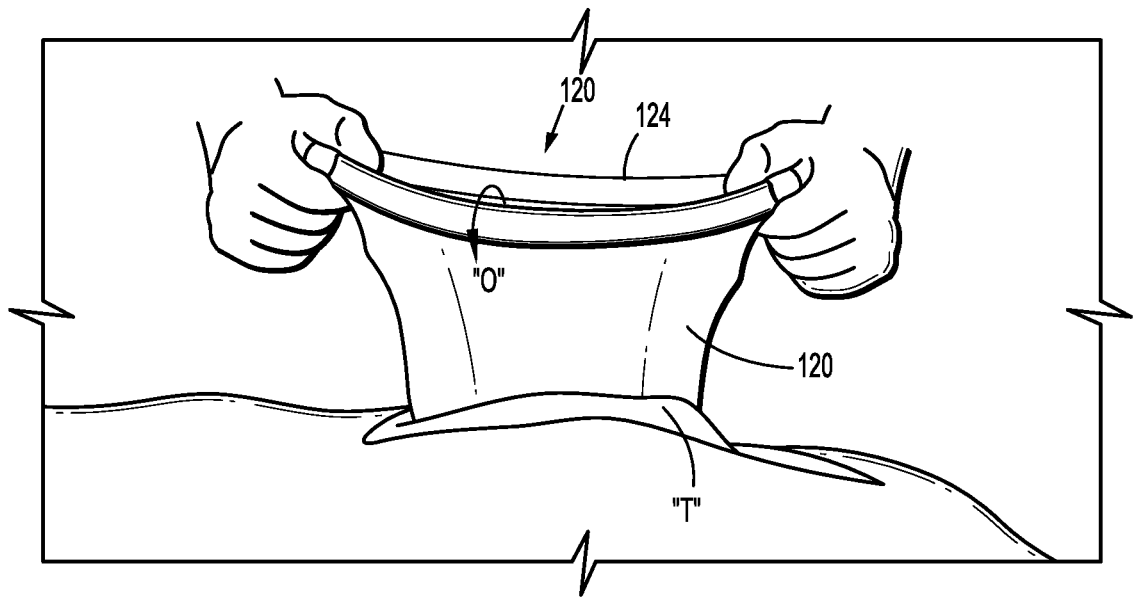
FIGS. 4 and 5 are perspective views of a sleeve assembly of the surgical access assembly of FIG. 1, illustrating use thereof.
Figure 5:
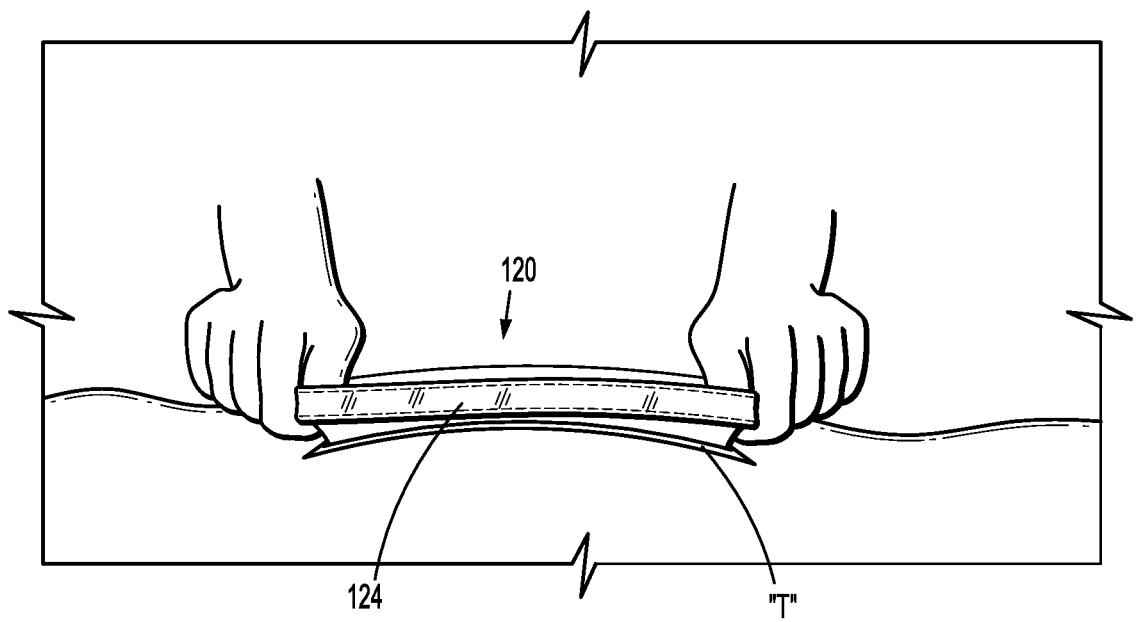

The sleeve 126 has elastomeric properties to facilitate securement of the sleeve assembly 120 to the opening in tissue "T" (FIG. 4). The proximal ring 124 is rollable to gather flexible sleeve 126 around the proximal ring 124. For example, the proximal ring 124 is rollable, e.g., in an outward direction "O" (FIG. 4) to shorten the sleeve 126 and in an inward direction to lengthen the sleeve 126, or vice versa. The sleeve 126 may be shortened such that the proximal ring 124 engages the outer epidermal tissue adjacent the opening in tissue "T," and the distal ring 122 positioned in the body cavity engages the internal peritoneal wall. In this manner, the sleeve assembly 120 is securely fixed to tissue "T."

Figure 3:
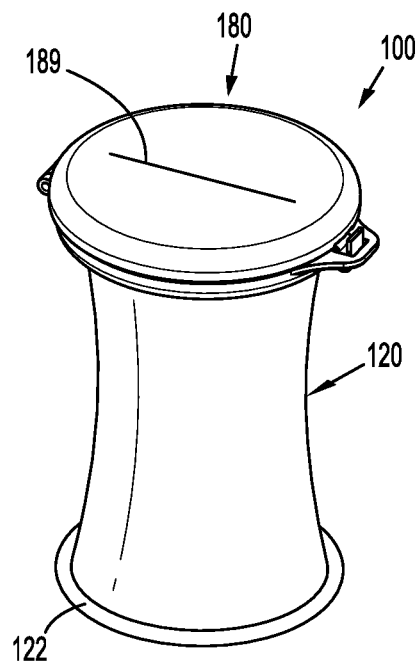
FIG. 3 is a perspective view of the surgical access assembly of FIG. 1, illustrating a closed state.

With continued reference to FIG. 3, proximal ring 124 may have, e.g., a kidney-shaped, cross-sectional profile. Kidney-shaped cross-section facilitates rolling of the sleeve 126 about the proximal ring 124. The distal ring 124, on the other hand, may be an O-ring having a circular cross-section. However, other cross-sectional profiles are also contemplated for the proximal and distal rings 122, 124. It is also envisioned that the O-ring may be an inflatable balloon. In addition, the proximal and distal rings 122, 124 may vary in size. For example, the dimensions of the proximal and distal rings 122, 124 may be selectively chosen to be larger than that of a desired opening. In this manner, the proximal and distal rings 122, 124 may have sufficient footing to maintain the elastic sleeve 126 that has been stretched.

By having dimensions of the proximal and distal rings 122, 124 larger than that of the desired the opening in tissue "T," the sleeve assembly 120 is adapted to retract/dilate the opening to a desired dimension. More retraction is possible through shortening of the sleeve 126 by rolling the proximal ring 124 outward, while less retraction is possible by rolling the proximal ring 124 inward. Reference may be made to U.S. Pat. No. 9,149,178, the entire contents of which are incorporated herein by reference, for a detailed description of the construction and operation of the sleeve assembly 120.

Figure 2:
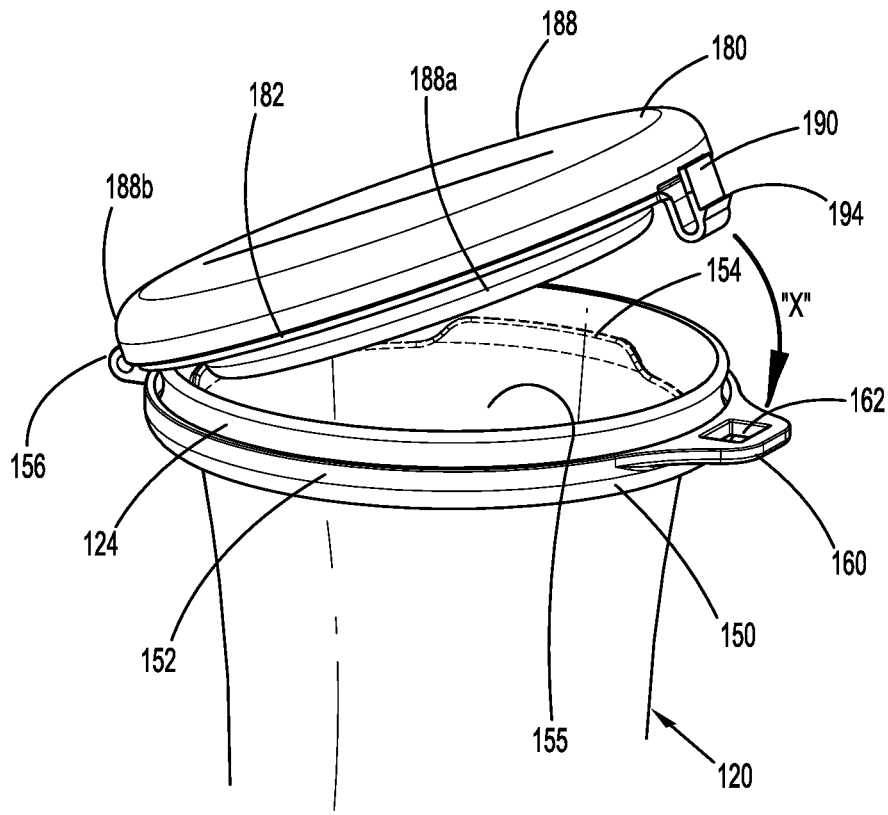
FIG. 2 is a partial perspective view of the surgical access assembly of FIG. 1.

With reference now to FIG. 2, the base member 150 is annular and has a circumferential groove (not shown) dimensioned to support the proximal ring 124 of the sleeve assembly 120 therein. The base member 150 includes lips 154 circumferentially arranged to concentrically support the proximal ring 124 of the sleeve assembly 120 within the circumferential groove. The base member 150 further includes a cup 156 configured to be hingedly coupled with the sealing assembly 180. In addition, the base member 150 further includes a coupling member 160 defining an aperture 162 dimensioned to releasably receive a hook 190 of the sealing assembly 180.

With continued reference to FIG. 2, the sealing assembly 180 includes a seal 188 and a frame 182 supporting the seal 188 thereon. The seal 188 may be formed of materials such as, e.g., gel or silicone, having sufficient compliance to form a seal about an object such as, e.g., a hand of a clinician, inserted therethrough. The seal 188 may define, e.g., a diametrically extending slit 189 (FIG. 3), to facilitate insertion of the object therethrough. The seal 188 may be over-molded onto the frame 182. The seal 188 includes a body portion 188a dimensioned to cover the aperture 155 defined by the base member 150 in a sealing relation, and an overhang portion 188b extending radially outward from the body portion 188a. The sealing assembly 180 may define a circumferential groove or a cutout (not shown) dimensioned to receive at least a portion of the proximal ring 124 of the sleeve assembly 120.

The frame 182 of the sealing assembly 180 includes the hook 190 configured to be received in the aperture 162 defined in the coupling member 160 of the base member 150, and a finger (not shown) configured to be hingedly coupled with the cup 156 of the base member 150. The finger may diametrically oppose the hook 190. The hook 190 includes a stop 194 configured to engage the coupling member 160 to secure the sealing member 180 with the base member 150. However, the hook 190 is deflectable such that when the hook 190 is pressed radially inward, the stop 194 may pass through the aperture 162 to transition the sealing assembly 180 to an open position (FIG. 1) from a closed position (FIG. 3).

In use, the peritoneal cavity (not shown) is insufflated with a suitable biocompatible gas such as, e.g., $CO_2$ gas, such that the cavity wall is raised and lifted away from the internal organs and tissue housed therein, thereby providing greater access thereto. The insufflation may be performed with an insufflation needle or similar device, as is conventional in the art. Either prior or subsequent to insufflation, an opening is made in tissue "T," the dimensions of which may be varied dependent upon the nature of the procedure.

With reference now to FIG. 4, compressed distal ring 122 (FIG. 3) of the sleeve assembly 120 is inserted through the opening in tissue "T". Subsequent to its insertion, the distal ring 122 expands to its expanded state beneath tissue "T." At this time, the proximal ring 124 may be rolled in the direction of arrow "O," such that the distal ring 122 engage the internal peritoneal wall, and the proximal ring 124 engages the outer epidermal tissue. In this manner, the sleeve 126 is securely disposed within the opening in tissue "T". Depending on the nature of the procedure being performed, the opening in tissue "T" may be retracted by further rolling the sleeve 126 about proximal ring 124.

At this time, the proximal ring 124 of the sleeve assembly 120 is placed in the circular groove of the base member 150 such that at least a portion of the proximal ring 124 extends proximally from the base member 150. Thereafter, the sealing member 180 may be hingedly coupled to the base member 150 by securing the finger of the frame 182 of the sealing member 180 to the cup 156 of the base member 150. Thereafter, the hook 190 diametrically opposing the finger may be inserted into the aperture 162 of the base member 150 to place the sealing member 180 in the closed position (FIG. 3). In this manner, a fluid-tight seal is established between the body cavity and the atmosphere.

At this time, one or more surgical objects including the clinician's hand may be inserted through the slit 189 defined in the seal 188 which maintains insufflation in the workspace by establishing a seal against the hand or a surgical object. With the object inserted through the surgical access assembly 100 and into the body cavity of the patient, the clinician may rotate the hand to a desired orientation with respect to tissue "T," while maintaining a fluid-tight seal between a body cavity of a patient and the atmosphere. Upon completing the surgical procedure, the user may remove the surgical access assembly 100 from the opening of the patient.

Figure 6:
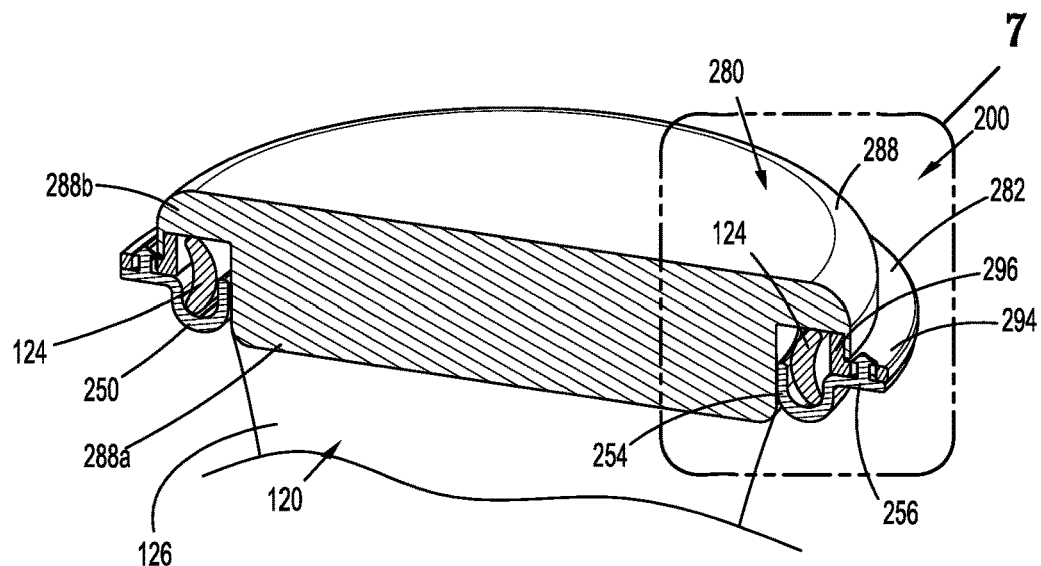
FIG. 6 is a partial perspective view of a surgical access assembly in accordance with another embodiment of the present disclosure with parts removed.
Figure 7:
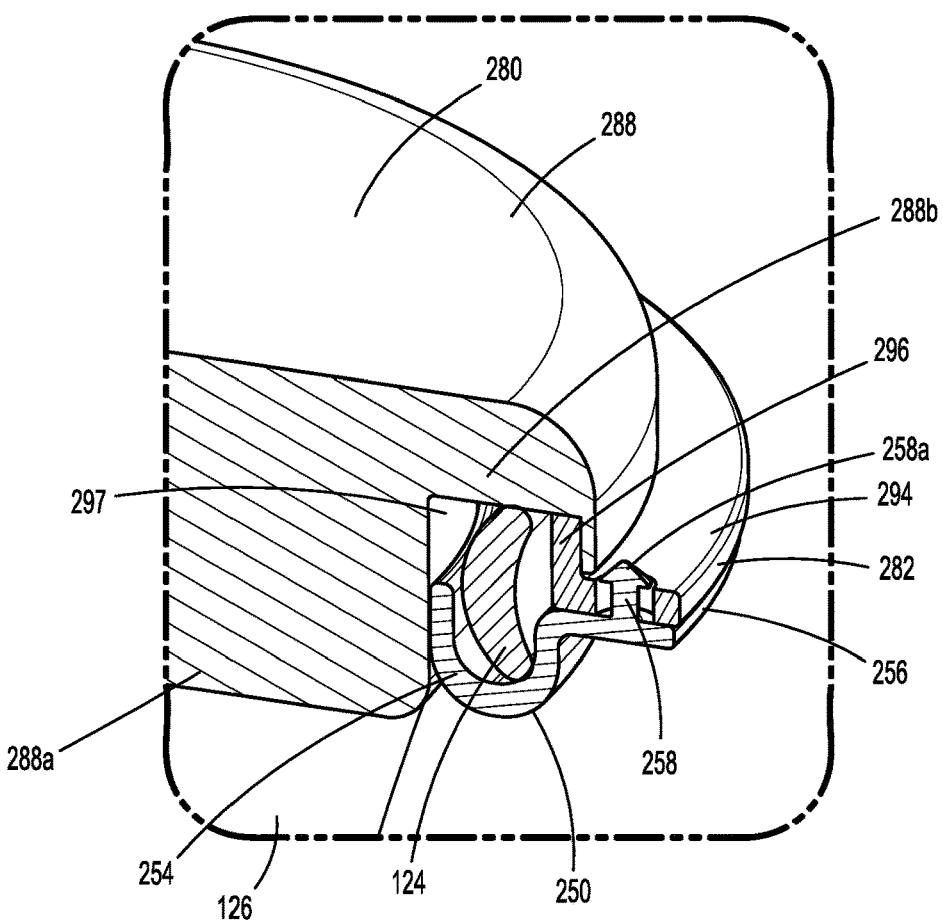
FIG. 7 is a partially enlarged perspective view of the surgical access assembly of FIG. 6.

With reference now to FIGS. 6 and 7, another embodiment of a surgical access assembly in accordance with another embodiment of the present disclosure is shown generally as a surgical access assembly 200. In the interest of brevity, portions of the surgical access assembly 200 substantially identical to the surgical access assembly 100 will not be described herein to avoid obscuring the present disclosure in unnecessary detail. The surgical access assembly 200 includes the sleeve assembly 120, a base member 250 configured to support the proximal ring 124 of the sleeve assembly 120, and a sealing assembly 280 configured to establish a fluid-tight seal between the body cavity and the atmosphere when an object such as, e.g., a hand of a clinician, is inserted therethrough.

With continued reference to FIGS. 6 and 7, the base member 250 is annular and includes a grooved portion 254 configured to support the proximal ring 124 of the sleeve assembly 120, and a base portion 256 extending radially outward from the grooved portion 254. The base portion 256 includes coupling members 258 configured to secure the seal member 280 to the base member 250. In particular, each coupling member 258 may include a rivet-like profile including a head portion 258a. The coupling members 258 may be evenly spaced apart about the base member 250.

The seal member 280 includes a frame 282 having an annular base 294 and a support 296 disposed radially inward of the annular base 294. The annular base 294 has a substantially flat surface extending radially outward such that when the annular base 294 is in superposed relation with the base portion 256 of the base member 250, the annular base 294 and the base portion 256 are in planar contact for enhanced stability and securement. The annular base 294 defines circumferentially arranged bores or slots 291 dimensioned to receive respective coupling members 258 of the base member 250. The coupling members 258 and/or the annular base 294 may be formed of compressible and/or resilient material to provide, e.g., snap-fit configuration, whereby when the base portion 256 and the annular base 294 are pressed together, the head portion 258a of the coupling member 258 having larger dimensions than a width of the slot 291 extends through the slot 291 and secures the annular base 294 to the base portion 256.

Figure 8:
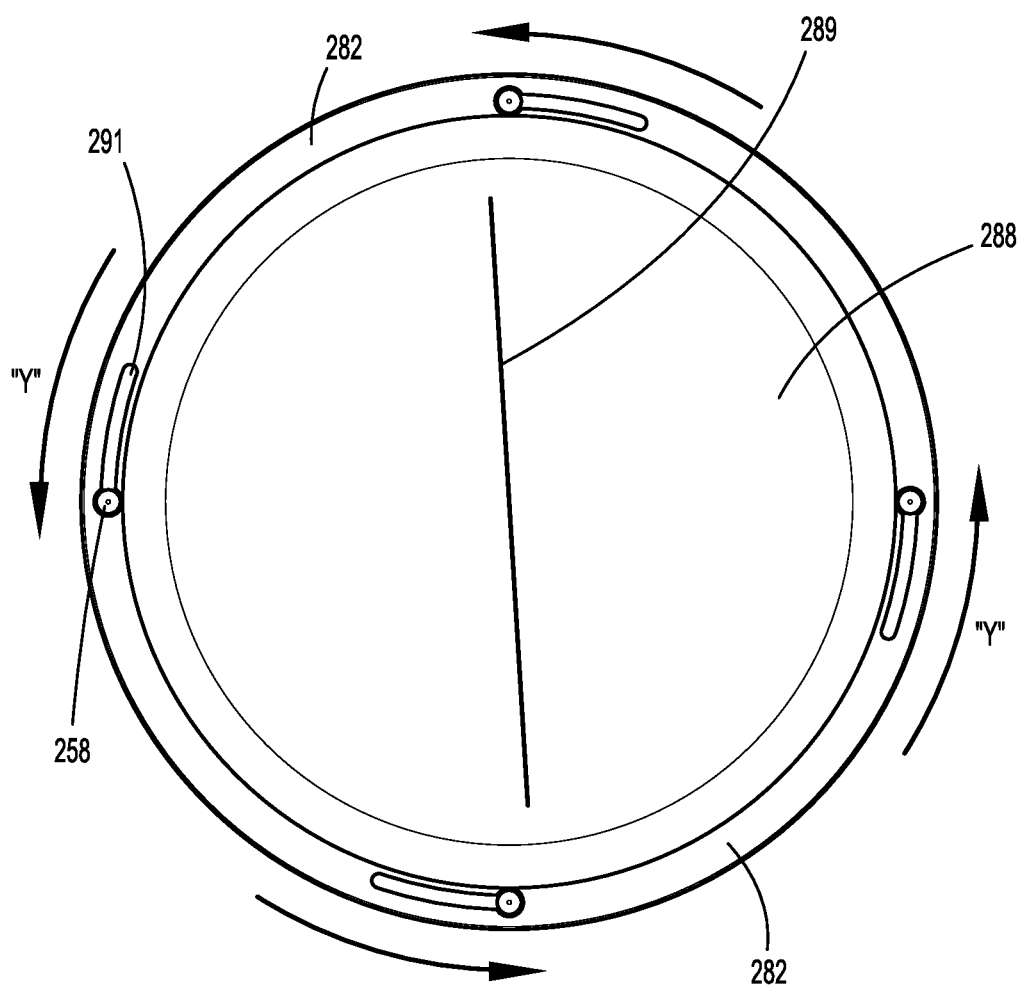
FIG. 8 is a top view of the surgical access assembly of FIG. 6.

With reference to FIG. 8, it is further contemplated that each slot 291 may be tapered, thereby providing a varying width in each slot 291. In this manner, after inserting the head portions 258a of the coupling members 258 through the respective slots 291 of the frame 282, the frame 282 may be rotated relative to the base member 250 (e.g., in the direction of arrow "Y") to further secure the frame 282 against the base member 250.

The sealing assembly 280 further includes a seal 288. The seal 288 may be formed of materials such as, e.g., gel or silicone, having sufficient compliance to form a seal about an object such as, e.g., a hand of a clinician, inserted therethrough. In particular, the seal 288 may be over-molded onto the support 296 of the frame 282. The seal 288 includes a body 288a disposed in the opening defined by the base member 250, and an overhang 288b extending radially outward from the body 288a such that the overhang 288b is over-molded onto the support 296 of the frame 282. Under such a configuration, the sealing assembly 280 defines a gap 297 between the body 288a and the support 296 in order to facilitate securement of the proximal ring 124 between the sealing assembly 280 and the base member 250. The seal 288 may define, e.g., a slit 289, dimensioned to receive an object such as, e.g., a hand of a clinician, inserted therethrough. The use of the surgical access assembly 200 is substantially identical to the use of the surgical access assembly 100 and, thus, will not be described herein.

With reference now to FIGS. 9-11, a sealing assembly and a base member in accordance with another embodiment of the present disclosure is shown generally as a base member 350 and a sealing assembly 380. In the interest of brevity, portions of the base member 350 and the sealing assembly 380 substantially identical to the base members 150, 250 and the sealing assemblies 180, 280 will not be described herein to avoid obscuring the present disclosure in unnecessary detail. The base member 350 and the sealing assembly 380 are configured for use with the sleeve assembly 120 (FIG. 1). The base member 350 is configured to support the proximal ring 124 of the sleeve assembly 120. The sealing assembly 380 is configured to establish a fluid-tight seal between the body cavity and the atmosphere when an object such as, e.g., a hand of a clinician, is inserted therethrough. The proximal ring 124 is releasably securable between the base member 350 and the sealing assembly 380.

With particular reference to FIG. 9, the base member 350 is annular and defines an opening 352. The base member 350 includes a grooved portion 354 configured to support the proximal ring 124 of the sleeve assembly 120. The grooved portion 354 includes an inner portion 355a having circumferentially arranged of lips 358 configured to retain the proximal ring 124 within the grooved portion 354, and an outer wall 355b having tabs 360 extending radially outward. For example, the outer wall 355b may include, e.g., two, tabs 360 diametrically opposing each other.

The sealing assembly 380 includes an annular frame 382 having an inner wall 394 defining a groove 396 dimensioned to slidably receive the corresponding tab 360 of the base member 350 such that the sealing assembly 380 and the base member 350 are rotatable relative to each other. The inner wall 394 further defines an axially extending notch 397 in communication with the groove 396. The axially extending notch 397 is dimensioned to lead the tab 360 of the base member 350 into the groove 396. Under such a configuration, when the tabs 360 are inserted into the respective axially extending notches 397 and the sealing assembly 380 is rotated relative to the base member 350, the sealing assembly 380 is securely coupled to the base member 350.

In this manner, the proximal ring 124 of the sleeve assembly 120 is securely interposed between the base member 350 and the sealing assembly 380. Optionally, the sealing assembly 380 may include external tabs 391 circumferentially arranged thereabout to enhance gripping by the clinician.

The sealing assembly 380 further includes a seal 388 formed of materials such as, e.g., gel or silicone, having sufficient compliance to form a seal about an object such as, e.g., a hand of a clinician, inserted therethrough. The seal 388 may be over-molded onto the frame 382. The seal 388 covers the opening 352 defined by the base member 350. The seal 388 may define a slit (not shown) dimensioned to receive an object such as, e.g., a hand of a clinician, inserted therethrough. The use of the base member 350 and the sealing assembly 380 is substantially identical to the use of the base members 150, 250 and the sealing assemblies 180, 280 of the surgical access assemblies 100, 200 and, thus, will not be described herein.

Persons skilled in the art will understand that the structures and methods specifically described herein and shown in the accompanying figures are non-limiting exemplary embodiments, and that the description, disclosure, and figures should be construed merely as exemplary of particular embodiments. For example, while the surgical access assemblies 100, 200 are shown for use in hand-assisted procedures, introduction of various types of instrumentation adapted for insertion through the sealing assembly 180, 280, 380, while maintaining a substantially fluid-tight interface about the instrument to help preserve the integrity of an insufflated workspace from gas and/or fluid leakage is further contemplated. Examples of instrumentation include, but are not limited to, clip appliers, graspers, dissectors, retractors, staplers, laser probes, photographic devices, endoscopes and laparoscopes, tubes, and the like.

It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical access assembly comprising:
  a sleeve assembly including a proximal ring, a distal ring, and a sleeve defining a passage therethrough, the sleeve extending between the proximal and distal rings;
  a base member including an annular body including a coupling member and lips, the annular body defining an opening in communication with the passage of the sleeve, and a circumferential groove configured to support the proximal ring of the sleeve assembly, the lips extending proximally from the annular body to retain the proximal ring within the circumferential groove of the annular body, the lips conforming to a curvature of the annular body, adjacent lips defining a gap therebetween; and
  a sealing assembly including an annular frame and a seal having a body dimensioned to cover the opening of the base member in a sealing relation and an overhang extending radially outwards from the body, the body and the overhang formed of a material having compliance to form a seal about an object;

wherein the coupling member of the base member releasably secures the sealing assembly to the base member, the annular frame of the sealing assembly configured to be in registration with the annular body of the base member such that the proximal ring is interposed between the base member and the sealing assembly.

2. The surgical access assembly according to claim 1, wherein the annular frame and the body of the seal define a gap therebetween, the gap dimensioned to receive at least a portion of the proximal ring of the sleeve assembly.

3. The surgical access assembly according to claim 1, wherein the lips are disposed radially inward of the proximal ring of the sleeve assembly.

4. The surgical access assembly according to claim 1, wherein the sealing assembly is hingedly coupled with the base member.

5. The surgical access assembly according to claim 4, wherein the annular frame of the sealing assembly includes a hook, and the annular body of the base member defines an aperture dimensioned to receive the hook.

6. The surgical access assembly according to claim 5, wherein the hook is deflectable such that the hook is selectably movable through the aperture of the base member.

7. The surgical access assembly according to claim 1, wherein the seal of the sealing assembly is formed of gel or silicone.

8. The surgical access assembly according to claim 1, wherein the proximal ring of the sleeve assembly has a kidney-shaped cross-section.

9. The surgical access assembly according to claim 1, wherein the sleeve of the sleeve assembly is rollable about the proximal ring.

10. The surgical access assembly according to claim 1, wherein the seal of the sealing assembly is over-molded on to the annular frame.

11. The surgical access assembly according to claim 1, wherein the overhang of the seal is proximal of the body of the seal.

* * * * *